United States Patent [19]

Kaplan et al.

[11] Patent Number: 5,810,869
[45] Date of Patent: Sep. 22, 1998

[54] METHODS FOR LOADING COAXIAL CATHETERS

[75] Inventors: Aaron V. Kaplan; Enrique J. Klein, both of Los Altos, Calif.

[73] Assignee: Localmed, Inc., Palo Alto, Calif.

[21] Appl. No.: 751,780

[22] Filed: Nov. 18, 1996

[51] Int. Cl.⁶ .................................................. A61M 25/18
[52] U.S. Cl. .......................... 606/194; 606/108; 604/96
[58] Field of Search .................................. 604/103, 283, 604/96; 606/194, 108

[56] References Cited

U.S. PATENT DOCUMENTS

| | | | |
|---|---|---|---|
| 4,551,146 | 11/1985 | Rogers | 604/283 X |
| 4,748,982 | 6/1988 | Horzewski et al. | 128/344 |
| 4,762,129 | 8/1988 | Bonzel | 128/344 |
| 4,911,163 | 3/1990 | Fina | 606/127 |
| 5,024,655 | 6/1991 | Freeman et al. | 604/103 X |
| 5,061,273 | 10/1991 | Yock | 606/194 |
| 5,180,367 | 1/1993 | Kontos et al. | 604/101 |
| 5,257,974 | 11/1993 | Cox | 604/96 |
| 5,263,945 | 11/1993 | Byrnes et al. | 604/283 |
| 5,266,073 | 11/1993 | Wall | 623/1 |
| 5,300,085 | 4/1994 | Yock | 606/191 |
| 5,318,529 | 6/1994 | Kontos | 604/96 |
| 5,336,178 | 8/1994 | Kaplan et al. | 604/53 |
| 5,498,240 | 3/1996 | Bagaoisan et al. | 604/96 |
| 5,501,668 | 3/1996 | Kontos | 604/96 |
| 5,536,250 | 7/1996 | Klein et al. | 604/96 |
| 5,562,620 | 10/1996 | Klein et al. | 604/96 |
| 5,567,203 | 10/1996 | Euteneuer et al. | 604/96 |
| 5,569,184 | 10/1996 | Crocker et al. | 604/53 |
| 5,607,406 | 3/1997 | Hernandez et al. | 604/264 |

FOREIGN PATENT DOCUMENTS

| | | | |
|---|---|---|---|
| WO 95/26773 | 10/1995 | WIPO | A61M 25/00 |
| WO 95/26777 | 10/1995 | WIPO | A61M 31/00 |
| WO 96/08286 | 3/1996 | WIPO | A61M 25/00 |
| WO 96/23542 | 8/1996 | WIPO | A61M 25/00 |

*Primary Examiner*—Michael H. Thaler
*Attorney, Agent, or Firm*—Townsend and Townsend and Crew LLP

[57] ABSTRACT

The catheter system comprises a balloon catheter having a removable hub. The hub is removed to permit loading of a sleeve catheter over the proximal end of the balloon catheter. The removable hub includes both a circumferential seal for preventing leakage of inflation medium from the hub and a mechanical interlock for axially securing the hub to the balloon catheter.

9 Claims, 8 Drawing Sheets

METHODS FOR LOADING COAXIAL CATHETERS

BACKGROUND OF THE INVENTION

1. Field of the Invention

The present invention relates generally to systems, devices, and methods for performing multiple, sequential intraluminal procedures. In particular, the method provides for the loading of a sleeve catheter over the proximal end of a balloon catheter, where the balloon catheter has removable proximal hubs.

In percutaneous transluminal angioplasty procedures, a catheter having an expansible distal end, usually in the form of a balloon, is positioned in a lumen of a blood vessel with the distal end disposed within a stenotic atherosclerotic region of the vessel. The expansible end is then expanded to dilate the vessel and, upon deflation and withdrawal, restores adequate blood flow through the diseased region. During dilatation, blood flow is interrupted, generally limiting inflation time to no more than 3 minutes.

While angioplasty has gained wide acceptance, it continues to be limited by two major problems, abrupt closure and restenosis. Abrupt closure refers to the acute occlusion of a vessel immediately after or within the initial hours following the dilatation procedure. This complication occurs in up to one of twenty cases and may result in myocardial infarction and death if blood flow is not quickly restored. Other acute complications, such as arterial dissections can be treated either by prolonged balloon inflations lasting more than 5 minutes or by placement of an intraluminal prosthesis usually called a stent. Prolonged balloon inflations require special angioplasty balloon catheters which allow for perfusion through or around the dilatation catheter during inflation.

Restenosis refers to the re-narrowing of an artery after an initially successful angioplasty. Occurring usually within the initial six months after angioplasty, restenosis afflicts up to 50% of all cases. That is, approximately one of every two or three patients will require additional revascularization procedures. Many different strategies have been tried unsuccessfully to reduce the restenosis rate, including mechanical (e.g., prolonged balloon inflations, stents, heated balloons, atherectomy, and laser) and pharmacologic (e.g., calcium antagonists, ace inhibitors, fish oils, steroids and anti-metabolic) approaches. A promising new strategy is to deliver a therapeutic agent directly to the arterial wall at the site of angioplasty. Several devices have been developed to deliver agent locally into the arterial wall. Similar to angioplasty balloon catheters, most drug delivery catheters interrupt blood flow to the distal myocardium, limiting the duration of time to deliver agent. Another promising strategy is to deliver stents to a vascular site following balloon angioplasty. A third strategy relies on prolonged balloon inflation with "perfusion" catheters which permit blood to flow distally while the balloon is inflated to reduce ischemia.

Until recently, the use of multiple modalities to treat a single lesion required the use of separate specialized catheters. For example, the localized delivery of therapeutic drugs following angioplasty first required the use of an angioplasty balloon catheter and then required the use of a separate drug delivery catheter. Similarly, stent placement following angioplasty required the use of a separate stent-delivery catheter following the initial angioplasty procedure. In some cases, the treatment of a single lesion required the use of two or more angioplasty balloon catheters, where a balloon having a larger inflated diameter would be employed when the earlier balloon(s) provided insufficient dilation of the blood vessel lumen. Also, balloon catheters with perfusion capabilities could be employed to do angioplasty and subsequent prolonged inflations, but these catheters (referred to as perfusion balloon catheters) were generally more complex, less trackable, and had a larger profile than comparable balloon angioplasty catheters not incorporating a perfusion feature. Thus, perfusion catheters can be less trackable and more costly than comparable angioplasty catheters.

To overcome at least some of the shortcomings involved with the use of separate, specialized catheters for performing post-angioplasty procedures, the use of sleeve catheters carrying various interactive devices and structures has been proposed. See, for example, U.S. Pat. No. 5,336,178, which describes the use of a sleeve catheter for delivering drugs over a balloon catheter. See also U.S. Pat. No. 5,266,073, which describes the use of a sleeve catheter for delivering a stent over a separate balloon catheter. See also copending applications Ser. No. 08/222,143, filed on Apr. 1, 1994, now U.S. Pat. No. 5,571,086, (with an equivalent application published as WO 95/26777) and Ser. No. 08/551,932, filed on Oct. 23, 1995, which describe the construction and use of sleeve catheters for providing a variety of treatment and diagnostic modalities over a conventional angioplasty balloon, including drug delivery, blood perfusion, stent delivery, ultrasonic imaging, and the like. Sleeve catheters having perfusion lumens are described in U.S. Pat. Nos. 5,562,620 and 5,536,250, PCT application WO 95/26773, and copending application Ser. No. 08/536,555. Sleeve catheters which can be placed over angioplasty balloons for increasing the effective balloon diameter are described in copending application Ser. No. 08/325,958 now U.S. Pat. No. 5,634,901.

While the sequential use of sleeve catheters for providing a wide variety of treatment and diagnostic modalities in combination with conventional balloon angioplasty and other base catheters is very promising, it suffers from certain drawbacks. In particular, the presence of a proximal hub on conventional balloon angioplasty catheters makes it difficult or impossible to load a sleeve catheter over the proximal end of the balloon catheter. Thus, the sleeve catheter must be loaded in a retrograde manner over the distal end of the balloon catheter, preventing in situ loading of the sleeve catheter when the balloon catheter is in the patient's vasculature. That is, the sleeve catheter can only be mounted on the balloon catheter either prior to the angioplasty procedure or after the balloon catheter has been withdrawn from the patient following the balloon angioplasty procedure. Pre-loading of the sleeve catheter can be disadvantageous in several respects. First, the sleeve catheter is consumed and must be disposed of regardless of whether it is actually used in the procedure. Second, the particular sleeve catheter must be selected prior to the angioplasty procedure, thus limiting flexibility and choice. Third, it may be desirable to employ two or more sleeve catheters sequentially, necessitating that the balloon catheter be withdrawn multiple times in order to effect mounting of the subsequent sleeve catheters. Loading of the sleeve catheter after introducing the angioplasty balloon (post-loading) is also disadvantageous. The need to withdraw the catheter requires extra time and can be cumbersome. It often involves the use of multiple balloons which require the use of additional equipment including exchange length wires.

The ability to maintain the balloon at the lesion site during the introduction of one or more sleeve catheters will overcome some or all of the disadvantages described above.

It has been previously suggested that the mounting of sleeve catheters coaxially over balloon catheters could be simplified by utilizing balloon catheters having removable proximal hubs. While such suggestions have been made, no specific systems, catheters, or methods have been developed to adequately implement such an approach. Moreover, the design of a balloon catheter having a removable hub is problematic in several respects. First, the hub must be easily mounted and removed since such steps may have to be repeated several times during any particular procedure. Second, a fluid-tight seal must be provided between the hub and the balloon inflation lumen in the catheter body. Angioplasty balloons are inflated to very high pressures, often above 20 atmospheres, and any leakage from the catheter system is unacceptable. Third, it is desirable that the catheter hub be firmly locked to the proximal end of the catheter. The high balloon inflation pressures result in significant axial forces on the proximal hub, and the catheter would fail if the hub became disengaged from the catheter body during a procedure. To date, no balloon catheter systems have been developed which adequately meet all of these requirements.

Additionally, post-loading of sleeve catheters over the proximal end of a balloon catheter presents unique demands on each of the components of the system. In particular, it is necessary that the relative dimensions of each of the components be adequately matched to facilitate such post-loading procedures. Both the lengths and the diameters of various system components must be properly selected in order to have integrated systems which facilitate such post-loading. To date, the requirements of the relative dimensions of the system components have not adequately been addressed.

Balloon catheters having removable proximal hubs are described in U.S. Pat. Nos. 5,501,668 and 5,318,529. The balloon catheters have integral or removable guide wire components, and the removable hub is provided to accommodate the particular catheter structure. In one embodiment of the '668 patent (FIG. 7), a removable hub is provided in a catheter with an integrated guide wire. In all embodiments of the '668 patent, the hub is held to the proximal end of the catheter body by a single compression fitting. While a compression fitting may be adequate to inhibit the leakage of inflation medium, it provides no positive mechanical interlock of the hub to the catheter body.

For these reasons, it would be desirable to provide improved systems, devices and methods for performing multiple, sequential intraluminal diagnostic and/or interventional procedures. It would be particularly desirable if such systems, devices and methods overcame at least some of the problems noted above. For example, it would be desirable to provide balloon catheters having improved removable hubs, where the hubs are more securely attached to the proximal end of a balloon catheter body. The balloon catheters having such hubs should be adapted for use with a wide variety of sleeve catheters, should be simple in construction, and should be capable of rapid deployment. In particular, the hub should be easily removable, leave a proximal end of the catheter body which can readily accommodate any desired sleeve catheter, and be readily replaceable after the sleeve catheter has been loaded coaxially over the catheter body. Catheter systems employing the balloon catheter should be provided where the relative dimensions of the balloon catheter, the associated sleeve catheter, and a guide wire may be selected to be compatible and to facilitate loading of the sleeve catheter over the proximal end of the balloon catheter while a guide wire is in place. The catheter should further be capable of being left in place over a guide wire while the sleeve catheter is being loaded thereover. At least some of the objectives should be met by each of the aspects of the present invention described hereinafter.

2. Description of the Background Art

Sleeve catheters for introduction over balloon catheters are described in U.S. Pat. Nos. 5,562,620; 5,536,250; 5,336,178; 5,266,073; and 5,257,974; and PCT Publications WO 95/26773; WO 95/26777; and WO 96/08286.

Balloon catheters having interchangeable proximal hubs are described in U.S. Pat. Nos. 5,501,668 and 5,318,529. A balloon catheter having a replacement shaft section is described in U.S. Pat. No. 5,498,240. A balloon catheter having separable reusable components is described in WO 96/23542.

Angioplasty catheters having shortened guide wire lumens which permit rapid exchange of the catheter over a guide wire are disclosed in U.S. Pat. Nos. 5,300,085; 5,061,273; 4,762,129; and 4,748,982.

Copending applications assigned to the assignee of the present application which disclose related subject matter include the following: U.S. Ser. No. 08/222,143 filed on Apr. 1, 1994; U.S. Ser. No. 08/241,428, filed on May 11, 1995; U.S. Ser. No. 08/325,958, filed on Oct. 20, 1994; U.S. Ser. No. 08/401,541, filed on Mar. 10, 1995; U.S. Ser. No. 08/461,222, filed on Jun. 5, 1995; U.S. Ser. No. 08/464,153, filed on Jun. 5, 1995; U.S. Ser. No. 08/473,800, filed on Jun. 7, 1995; and U.S. Ser. No. 08/551,932, filed on Oct. 23, 1995, and U.S. Ser. No. 08/704,801, filed on Aug. 26, 1996. The full disclosures of each of these applications is incorporated herein by reference.

SUMMARY OF THE INVENTION

The present invention provides improved systems, devices, and methods for coaxially introducing or loading sleeve catheters over balloon catheters before, during, or after the performance of balloon angioplasty or other interventional or diagnostic procedures. In particular, the present invention allows post-loading of the sleeve catheter over the proximal end of a balloon catheter while the balloon catheter remains in situ in a patient's vasculature or other luminal system. Such post-loading is achieved by removing a removable proximal hub from the proximal end of the balloon catheter while the balloon catheter remains in situ, introducing a central lumen of the sleeve catheter over the proximal end of the balloon catheter (from which the removable hub has been removed), and advancing the sleeve catheter distally until it reaches a desired target site. Usually, the sleeve catheter will have an interactive component thereon which interacts in some way with the balloon of the balloon catheter. In such cases, the interactive component will be aligned over the balloon, and the balloon inflated to provide the desired interaction.

The present invention is advantageous in a number of respects. First, the present invention provides for a fluid tight seal between the removable hub and the inflation lumen in the balloon catheter, thus preventing unintended leakage of inflation medium during any portion of the procedure. Second, the present invention provides a mechanically secure interlock between the removable hub and the body of the balloon catheter to assure that the removable hub is not accidentally dislodged during performance of the procedure. In particular, the fluid seal and the mechanical interlock will preferably but not necessarily be provided by separate mechanisms within the catheter system. Third, the present invention provides for very simple removal and remounting of the removable hub on the proximal end of the catheter. In particular, insertion of the balloon body into the removable hub is completed when the catheter hits a mechanical stop point within the hub, thus assuring that the mounting of the hub on the catheter body is complete and is repeatable every time. Fourth, the balloon catheter and removable hub are useful with a wide variety of sleeve catheters intended for different purposes, as described in more detail below. Fifth, the present invention provides for methods and systems which assure the proper selection of system components for compatibility. In particular, the present invention allows for the selection of combinations of the balloon catheter, sleeve catheter, and guide wire dimensions so that post-loading of the sleeve catheter over the balloon catheter and guide wire is facilitated. Each of these advantages will be provided by one or more of the following aspects of the present invention.

In a first aspect of the present invention, the catheter system comprises an elongate catheter body having a distal end and a proximal end, and a hub removably securable over the proximal end of the catheter body. The catheter body has an inflatable balloon near its distal end and an inflation lumen which extends from the balloon over the entire distance of the catheter body to the proximal end. The catheter body further has a guide wire lumen which extends from the distal end to a proximal port which is spaced distally from the proximal end of the catheter body. As will be seen hereinafter, the guide wire exits the catheter body and bypasses the removable hub altogether.

In the first aspect of the present invention, the hub is secured to the proximal end of the catheter body with both a circumferential seal and a mechanical interlock. The circumferential seal may be an O-ring or other compressive seal which permits axial introduction and sliding of the catheter body therethrough. The mechanical interlock is disposed on the hub, the catheter body, or both, and selectively engages (or disengages) the catheter body and axially locks (or unlocks) the catheter body to the hub. Separating the fluid seal from the mechanical interlock is particularly advantageous since neither the fluid seal nor the mechanical interlock are compromised, as was the case with certain prior removable hub catheter embodiments. In some embodiments, however, the mechanical interlock can be provided in part by the compressive seal by including a surface feature or anchor on the catheter body which is engaged by the compressive seal to lock the hub to the catheter.

In the exemplary embodiment, the removable hub comprises a cylindrical block having a central passage therethrough which defines an inflation chamber. The circumferential seal is disposed at a distal end of the inflation chamber and an inflation port is disposed at a proximal end of the block. The mechanical interlock is preferably a mechanism which circumferentially grips an outer surface of the catheter body, more preferably a modified outer surface as described below. For example, the mechanism may comprise a radially constrictable distal extension on the cylindrical block and having a passage aligned with the central passage in the block. A slider is mounted on the block and has a proximally retracted position where the distal extension is not constricted and a distally extended position where the slider constricts the distal extension. Preferably, the distal extension will have a surface feature, such as serrations, which grip the outer surface of the catheter body when the extension is constricted. More preferably, the elongate catheter body will have an anchor feature on its outer surface, which anchor feature mates with the surface feature on the distal extension.

The catheter system may further comprise a sleeve catheter having a distal end, an interactive device which interacts with the balloon, a proximal end, and a central lumen extending from a distal port for the balloon catheter to a proximal port for the balloon catheter. The system may still further comprise a guide wire for introducing the balloon catheter through the vasculature or other luminal system. Preferably, the balloon catheter has a length $L_{BC}$ and the guide wire has a length $L_{GW}$, where the guide wire is longer than the balloon catheter (e.g., $L_{GW} \geq L_{BC}+10$ cm). Usually, the central lumen of the sleeve catheter has a length $L_{SC}$ in the range from 25 cm to 35 cm. The length of the balloon catheter $L_{BC}$ with the hub removed is preferably in the range from 120 cm to 200 cm, more preferably from 155 cm to 165 cm, and the length of the guide wire $L_{GW}$ is in the range from 130 cm to 230 cm, more preferably from 175 cm to 185 cm. The sleeve catheter will typically have a total length from its proximal length to its distal end in the range from 100 cm to 180 cm, preferably from 125 cm to 145 cm.

In a preferred feature of the catheter system, an elongate catheter body has an outer diameter which is reduced in the region proximal to the proximal guide wire port. Usually, the reduction of the diameter will be at least 25%, preferably being at least 30%. As will be described in greater detail hereinafter, the reduction in diameter is advantageous since it facilitates passage of the guide wire on the exterior of the balloon catheter body through the central lumen of the sleeve catheter.

In a second aspect, a catheter system according to the present invention comprises an elongate catheter body having a removable hub, a sleeve catheter, and a guide wire. The balloon catheter has a length $L_{BC}$ and the guide wire has a length $L_{GW}$, where $L_{GW}$ is greater than $L_{BC}$ by at least 10 cm ($L_{GW} \geq L_{BC}+10$ cm). The preferred dimensional parameters for each of the system components are the same as set forth above with respect to the first catheter system of the present invention. The catheter system having components with these dimensional relationships may optionally be combined with the removable hub having a separate fluid seal and mechanical interlock.

In a third aspect of the present invention, a removable hub comprises a hub body having an inflation chamber, a central passage, and an inflation port. The inflation port is connected to deliver inflation media to the chamber, and a circumferential seal is disposed in the catheter passage to seal about the proximal end of a balloon catheter body which is introduced therethrough. A mechanical interlock is also provided on the hub body and selectively engages the catheter body to axially lock the catheter body relative to the hub. In this way, the hub can be mounted on the proximal end of a separate balloon catheter in a manner which assures both sealing of an inflation lumen and a mechanical locking onto the catheter. The preferred features of the removable hub are generally as set forth above in connection with the first catheter system of the present invention.

In an exemplary embodiment, the circumferential seal can be an axially compressive seal, such as a Touhy-Borst seal or a modified O-ring. In such embodiments, the hub body will comprise a mechanism for axially compressing the seal, such as a tightening screw, to radially constrict the seal about the catheter body. Locking of the hub to the catheter can be further enhanced by roughening or otherwise texturing the outer surface of the catheter body in the region engaged by the axially compressive seal to enhance the frictional locking.

In a fourth aspect of the present invention, an improved balloon catheter comprises an elongate catheter body having a distal end and a proximal end. A balloon is disposed near the distal end and an inflation lumen extends from the balloon fully to the proximal end of the catheter. The balloon catheter does not include a removable hub, but instead has an anchor feature formed in the catheter body near the proximal end to permit mounting of a removable hub, such as the removable hub described above. The anchor feature does not radially protrude above the outer surface of the catheter body to any substantial extent, typically extending above the surface by a distance no greater than 10% of the radius of the catheter body, preferably no greater than 5%, and most preferably not protruding at all. In this way, sleeve catheters can be loaded coaxially over the proximal end of the catheter body (and usually simultaneously over an adjacent guide wire having a diameter of 0.014 in. as well) without substantial interference from the features and components on the catheter body intended to secure a removable hub.

In the exemplary embodiment, the surface feature comprises circular or helical surface serrations formed in the catheter body which permit gripping by the removable hub. It will be appreciated, however, that a wide variety of other surface features could be provided, such as grooves, indentations, slots, apertures, pins, or the like. Preferably, the catheter body will also have an outer diameter over the region which is proximal to the proximal guide wire port which is less than the maximum width, e.g. diameter, distal to the proximal port. Usually, the outer diameter is reduced by at least 25%, preferably by at least 30%.

The present invention still further provides a first method for loading a sleeve catheter over a balloon catheter. The method comprises providing a balloon catheter as generally described in connection with the first system of the present invention. The method further comprises providing a sleeve catheter as generally described in connection with the first system of the present invention. After removing the hub from the balloon catheter, the distal end of the sleeve catheter is advanced over the proximal end of the balloon catheter (and optionally a guide wire) so that the proximal end of the balloon catheter emerges from the proximal balloon catheter port on the sleeve catheter. A removable hub is then positioned over the proximal end of the balloon catheter, where the catheter passes through a circumferential seal in the hub. A locking element on the hub is then engaged against the catheter body to axially lock the hub relative to the balloon catheter.

Preferably, the locking step comprises constricting a portion of the hub circumferentially about the catheter body, where the constricted portion usually comprises a surface feature which grips the surface of the catheter body when constricted thereabout. More preferably, the catheter body will comprise an anchor feature which interlocks with the surface feature on the removable hub. In the exemplary embodiment, both the surface feature and the anchor feature comprise circular surface serrations which interlock when the removable hub is constricted.

In another aspect of the method of the present invention, the relative lengths of the sleeve catheter and balloon catheter may be selected based on the maximum expected length ($L_{SC}$) of the sleeve portion of the sleeve catheter and the insertional length ($L_V$) of the balloon catheter in the vasculature. The balloon catheter must have a sufficient length to protrude from the entry (proximal end) of the guide catheter even when the balloon catheter is advanced distally to the maximum expected extent. Thus, the length of the balloon catheter must be greater than the total of the insertional length $L_V$ and sleeve length $L_{SC}$ (i.e. the length of the sleeve portion of the sleeve catheter), preferably being greater than $L_V+L_{SC}$ by at least 5 cm, preferably 10 cm. The method further permits choosing a guide wire length. Preferably, the guide wire will be longer than the balloon catheter length $L_{BC}$ by at least 10 cm ($L_{GW} \geq L_{BC}+10$ cm).

DETAILED DESCRIPTION OF THE SPECIFIC EMBODIMENTS

The present invention provides systems, devices and methods for performing multiple, sequential intraluminal procedures on a patient as part of therapeutic or diagnostic treatment. By "intraluminal," it is meant that the procedures occur at a target location within a body lumen, usually being within the patient's vasculature, more usually being within the arterial system, including the coronary arteries, the peripheral arteries, and the cerebral arteries. The apparatus of the present invention, however, are not limited to use in the vascular system, and may also be advantageously employed in other body structures, including the prostate via the prostatic urethra, (e.g. to treat benign prostatic hypertrophy, prostatitis, and adenocarcinoma), the fallopian tubes via its lumen (to treat strictures), brain parenchyma (to treat Parkinson's disease), and the like.

The "target site" within the body lumen will usually be diseased or be suspected of being diseased. In the case of vascular treatment, the target locations will usually be stenotic regions where blood flow is restricted as a result of atheromatous deposits or plaque. Diseased sites within other body lumens are well-known and described in the medical literature.

By "multiple" procedures, it is meant that at least two interventional procedures will be performed as part of a single clinical treatment. Interventional procedures may be therapeutic and may include revascularization techniques, such as balloon angioplasty (with or without perfusion), laser angioplasty, ultrasonic angioplasty, atherectomy, and the like; drug delivery procedures; stent placement procedures; axial scoring or slitting of plaque prior to dilatation by balloon angioplasty; and the like. Interventional procedures may also be diagnostic including imaging, particularly ultrasonic imaging, angioscopy, contrast delivery, and the like. Usually, at least one procedure will include balloon angioplasty.

By "sequential," it is meant that one procedure will be performed followed by another while the balloon catheter (and usually a guide wire) remains in place. The procedures may be performed in any order, with or without repetitions. In the preferred case of intravascular treatment, at least one of the procedures will usually be therapeutic, more usually being balloon, laser or ultrasonic angioplasty, or atherectomy, while the other procedure may be therapeutic or diagnostic, usually being drug delivery, stent placement, balloon enlargement, prolonged balloon inflation with perfusion following angioplasty, or imaging.

The methods of the present invention will utilize both a balloon catheter and a sleeve catheter which is slidably received over the balloon catheter. The balloon catheter will comprise a catheter body having a proximal end and a distal end. An inflatable balloon will be disposed at or near the distal end, and an inflation lumen will extend through the catheter body from the balloon to the proximal end thereof. Preferably, the catheter body with an internal inflation lumen terminating in an open port at the proximal end of the catheter body will mate with the removable hub, as described in more detail hereinafter. The catheter body will usually also include a guide wire lumen through a portion thereof. The guide wire lumen will begin at the distal tip of the catheter body, usually passing through the balloon (but optionally passing over the balloon), and will extend some length in the proximal direction down the catheter body, terminating in a proximal port spaced distally from the proximal end of the catheter body. The catheter may be configured as a rapid exchange catheter, such as those described in U.S. Pat. Nos. 5,549,556; 5,300,085; 5,061,273; and 4,762,129. Alternatively, the guide wire lumen may extend down substantially the entire length of the catheter body, terminating a short distance from the proximal end, typically being at least 5 cm from the proximal, usually being in the range from 5 cm to 20 cm from the proximal end. In all cases, the guide wire lumen will terminate prior to the proximal end of the catheter body, and the guide wire will not pass through the removable catheter hub.

The sleeve catheter may be any of the catheter types discussed in the Background section hereinabove and will include at least a distal region or segment which is adapted to be received over the balloon catheter. In some cases, most or all of the length of the sleeve catheter will be received over the balloon catheter. The distal region or segment is usually provided with an interactive capability selected to interact with or complement the balloon of the balloon catheter. For example, the sleeve could provide blood perfusion lumens that can establish perfusion flow past a balloon inflated within the sleeve. Alternatively, it may be advantageous to provide an imaging sleeve catheter surrounding the angioplasty catheter, where the imaging capability can help assess the stenotic region during the procedure in order to provide more effective treatment. In such case, the two catheters need not be aligned. Drug delivery sleeve catheters are particularly useful to treat a target location after an angioplasty procedure in order to inhibit abrupt closure and/or restenosis. Radially expansible sleeve catheters permit delivery and subsequent placement of stents and grafts in combination with balloon angioplasty catheters. Alternatively, radially expandable sleeve catheters may carry cutting blades or other elements which may be deployed to score arterial plaque prior to balloon angioplasty. In some cases, the interactive device of the sleeve catheter may be the sleeve itself, where the thickness of the sleeve portion acts as an "enlargement membrane" and is relied on for increasing the effective diameter of a balloon when the balloon is inflated therein at a treatment site.

The sleeve catheter of the present invention will comprise a catheter body having a proximal end and a distal end. At least a distal region or segment of the catheter body will be adapted to slidably receive the proximal end of the balloon catheter (and usually on adjacent guide wire), where the balloon catheter body will have a maximum outer diameter in the range from 0.5 mm to 2.5 mm, more usually from 0.75 mm to 2 mm. Often it will be desirable to decrease the diameter of the balloon catheter over the portion proximal to the proximal guide wire port. The above dimensions are thus the maximum expected diameters. Usually, the body of the sleeve catheter (or a distal region or segment thereof) will be provided by a discreet tubular segment having a continuous lumen therethrough. In some cases, the tubular segment will be relatively short and attached at its proximal end to a shaft or other support structure having an outer diameter which is substantially less than that of the tubular segment, usually being no more than one-half of that of the tubular segment, preferably being no more than 40% of the tubular segment, more preferably being no more than 30% of the tubular segment. The distal region or segment, however, need not be formed separately from the remainder of the catheter body. In other cases, the catheter body will be a continuous structure or extrusion, which may have a substantially constant diameter along its length.

The total length of the sleeve catheter body will generally be in the range from 100 cm to 200 cm, preferably from 130 cm to 150 cm. In the short sleeve embodiments (e.g., FIG. 8), the proximal region of the catheter body will usually be in the form of a shaft having a length in the range from 100 cm to 175 cm. The proximal region of the catheter body, particularly when it is in the form of a separate shaft, will usually have a diameter smaller than that of the distal region or segment, typically in the range from 0.3 mm to 2 mm, usually from 0.5 mm to 0.75 mm. The catheter body (at least the distal region thereof) may be composed of a wide variety of biologically compatible materials, typically being formed from natural or synthetic polymers, such as polyvinylchloride, polyurethanes, polyesters, polyethylenes, polytetrafluoroethylenes (PTFE's), nylons, and the like.

The proximal shaft will usually comprise a small diameter rod or tube, with an outside diameter in the range set forth above. The rod or tube should have sufficient flexibility to be introduced through relatively non-tortuous regions of the vasculature while providing sufficient column strength to allow axial translation of the distal region of the catheter body through the more tortuous regions of the vasculature while positioned over the base catheter. The shaft will usually be composed of a metal, such as stainless steel, nickel-titanium alloy, hard plastic, reinforced plastic, or similar material providing good flexibility combined with good column strength. For example, a stainless steel rod, wire or hypotube could be used as the shaft, optionally covered with a polymeric sleeve or sheath. A lumen may be provided in the shaft, e.g., by utilizing a hypotube as the shaft or by forming a lumen as part of the polymeric sleeve or sheath. In the latter case, the lumen may be an annular lumen formed by using a sleeve which has an inner diameter larger than the outer diameter of the stainless steel rod or wire. Alternatively, the sleeve or sheath can have two or more lumens, where one lumen receives an internal rod, wire, or hypotube, and the other lumen(s) provide for access between the proximal end and the distal end of the proximal shaft. Access is useful for delivering and/or aspirating fluids, accommodating electrical leads, mechanical actuating wires, etc.

In preferred embodiments of the sleeve catheter of the present invention, at least a portion of the distal region or segment will be radially expansible to permit expansion of a balloon on the base catheter therein. The radially expansible portion may be provided by a variety of specific designs which permit both placement of the catheter body thereover and internal inflation of a balloon on a base catheter to permit radial expansion of the catheter body. Usually, the catheter body will have a relatively thin wall, which retains sufficient column strength to permit positioning of the catheter body over the balloon catheter, as described in more detail below.

When intended for placement over a conventional balloon angioplasty catheter, the distal region or segment of the catheter body will be sized to receive the balloon after it has been inflated and deflated. Since the balloon will seldom fold down to its original profile, the lumen diameter of the distal region or segment of the catheter body will have to be sized slightly larger than would otherwise be the case. Optionally, catheters having specific lumen diameters may be provided to correspond to differently sized balloon angioplasty catheters so that the treating physician will have a number of sleeve catheters according to the present invention to be used with different balloon angioplasty catheters. Alternatively, a single, large-sized sleeve catheter can be provided for use with a number of different angioplasty catheters having different balloon diameters. As a compromise, two or several different sleeve catheter sizes may be provided in an inventory to accommodate balloon angioplasty catheters having balloon diameters falling within certain ranges, e.g., large, medium and small, etc.

The radially expansible portion of the tubular catheter body may be formed in a variety of ways. For example, it may be defined by forming a plurality of axial slits in the tubular wall of the catheter body. The slits move circumferentially apart as the body is radially expanded by inflation of a balloon therein. Alternatively, the expansible portion may be formed by fabricating the tubular body at least in part from an elastomeric material which permits expansion. In another preferred embodiment, an axially split tubular catheter body is modified by the inclusion of non-distensible or elastomeric webs between adjacent axial segments. The axial segments resulting from splitting of the tubular body provide sufficient column strength, while the web portions fully contain the balloon within the lumen of the catheter body even after full expansion. The use of non-distensible webs can further be relied on to limit maximum balloon expansion, if so desired. The length of the radially expansible portion will typically be somewhat greater than that of a conventional angioplasty balloon of the balloon catheter in order to accommodate expansion of the balloon therein.

Typically, the length will be in the range from 1 cm to 5 cm, preferably from 2 cm to 4 cm, depending on the length of the balloon.

Often, two or more sleeve catheters having the same or a different function may be used sequentially in the course of a single procedure. In such cases, the ability to leave the balloon catheter (and usually the guide wire) in place at the target site in the vasculature and exchange successive sleeves over the balloon catheter is of great advantage.

Figure 1:
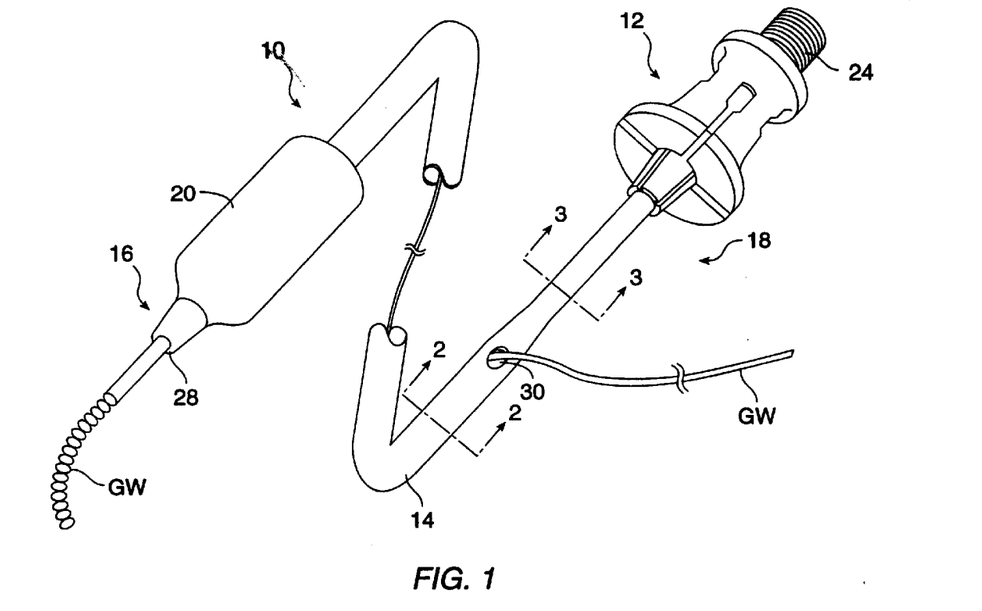
FIG. 1 is a perspective view of a balloon catheter having a removable hub according to the present invention, mounted over a guide wire.
Figure 2:
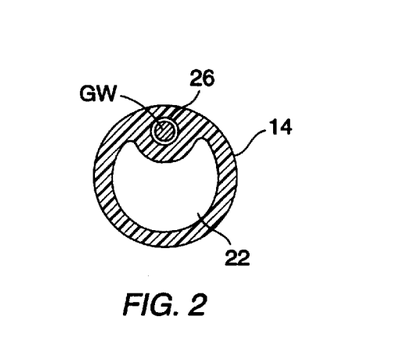
FIG. 2 is a cross-sectional view taken along line 2—2 of FIG. 1.
Figure 3:
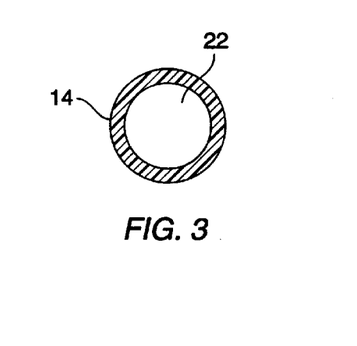
FIG. 3 is a cross-sectional view taken along line 3—3 of FIG. 1.

A balloon catheter 10 having a removable hub 12 constructed in accordance with the principles of the present invention is illustrated in FIGS. 1–3. The balloon catheter 10 comprises an elongate catheter body 14 having a distal end 16 and a proximal end 18. An inflatable balloon 20 is mounted on the distal end of the catheter body 14 and an inflation lumen 22 (FIGS. 2 and 3) extends through the catheter body 14 from the balloon 20 to the proximal end 18. As described in more detail hereinafter, the inflation lumen 22 is connected through an inflation port 24 on the removable hub 12 when the hub is connected to the catheter body. The catheter body 14 further includes a guide wire lumen 26 (FIG. 2) extending from the distal tip 28 through a distal portion of said body. The guide wire lumen 26 terminates at a proximal guide wire port 30, so that a guide wire GW passes out of the catheter body 14 distal to the proximal end where the removable hub 12 is removably mounted. In a specific aspect of the present invention, the diameter of the catheter body 14 may be reduced in the region proximal to port 30 (as shown in FIG. 3) relative to the distal portion (as shown in FIG. 2). Such reduction in diameter facilitates accommodation of the catheter body 14 and guide wire GW parallel to the proximal region of the catheter body in the guiding catheter as well as when the sleeve catheter is introduced thereover, as illustrated in FIGS. 3A and 3B.

Figure 3A:
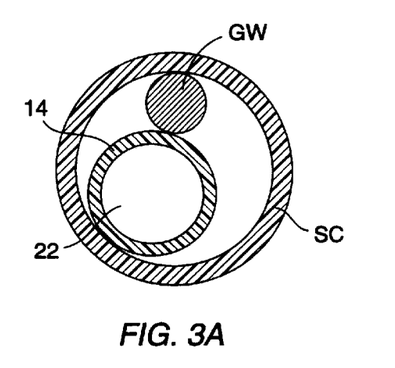
FIGS. 3A and 3B are cross-sectional views showing the balloon catheter body within the lumen of a sleeve catheter.
Figure 3B:
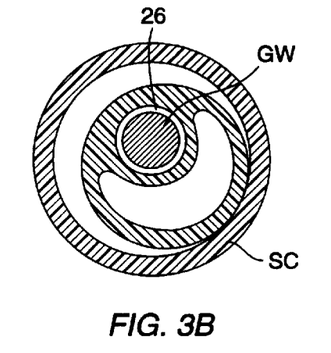

FIGS. 3A and 3B correspond generally to the cross-sectional views of FIGS. 3 and 2, respectively, except that the balloon catheter body 14 is shown within the lumen of a sleeve catheter SC. The ability of the reduced diameter portion of the catheter body 14 to accommodate the guide wire GW as it travels outside of the catheter body can clearly be seen in FIG. 3A.

Figure 4:
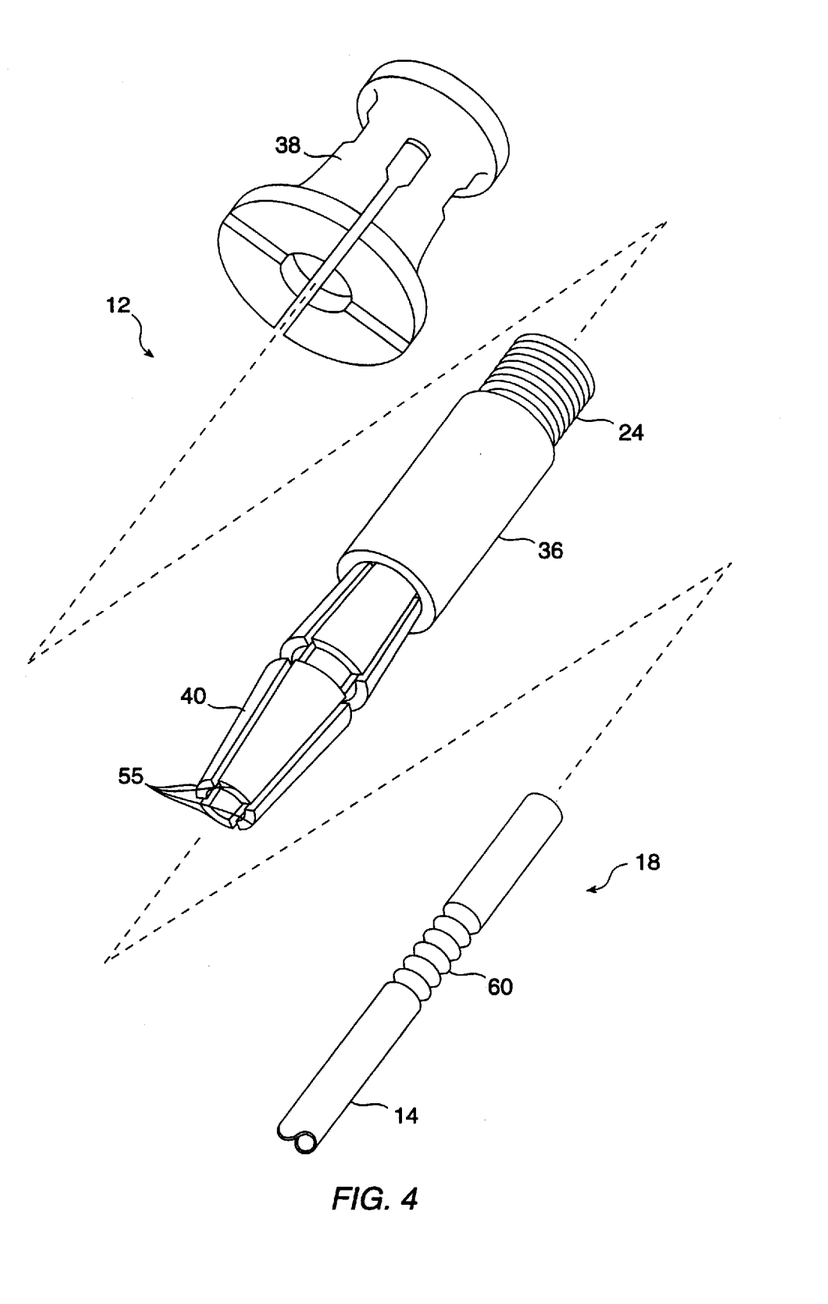
FIG. 4 is an exploded view of the proximal end of the balloon catheter of FIG. 1, illustrating the block and slider components of the removable hub.
Figure 5:
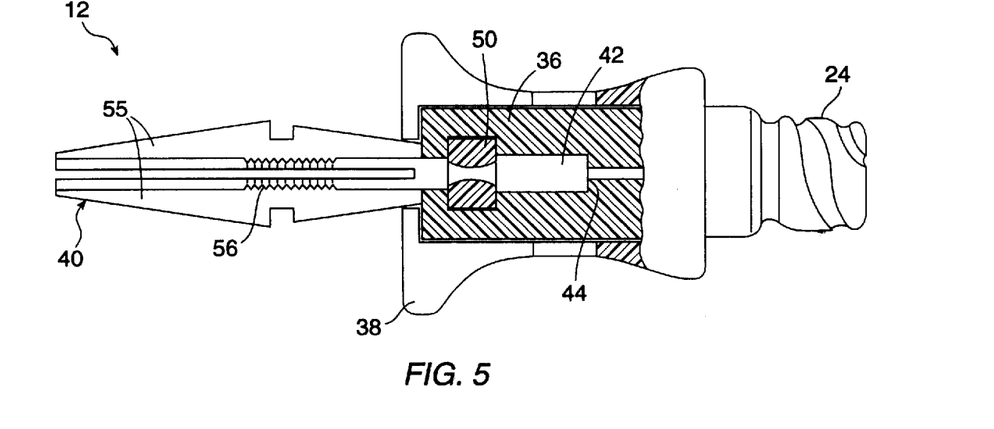
FIG. 5 is a partial cross-sectional view of the removable hub shown with the slider retracted and in the absence of a balloon catheter.
Figure 6:
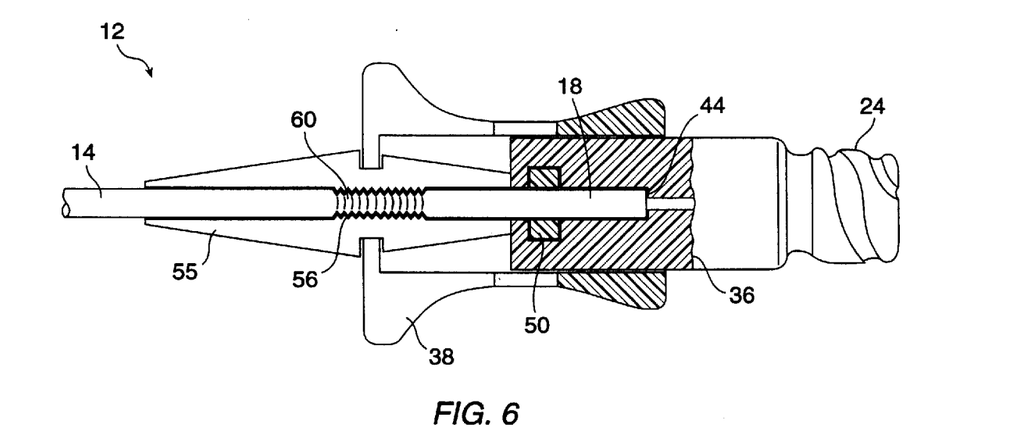
FIG. 6 is a partial cross-sectional view of the slider FIG. 5 shown with the slider distally advanced and the proximal end of the balloon catheter gripped therein.

Referring now to FIGS. 4–6, the removable hub 12 comprises a block 36, a slider 38, and a distal extension 40 attached to the distal end of the block 36. The block 36 includes a central passageway 42 defining an inflation chamber which receives proximal end 18 of the catheter body 14, as shown in FIG. 6. The central passage 42 includes a shoulder 44 which acts as a stop member (mechanical stop) for the proximal end 18 of the catheter body. In use, the catheter body 14 is inserted through the distal extension 40 and into the central passage 42 until the user can feel that it has reached the shoulder 44. Thus, the user knows that the catheter body 14 has been fully inserted into the removable hub 12, and the chance of accidental partial insertion of the catheter is significantly reduced. It will be appreciated that other mechanical features can be used as the stop member, such as pins, wires, screens, and the like.

A circumferential seal in the form of elastomeric sealing member, e.g. an O-ring a similar seal 50, is disposed within the central lumen, preferably near a distal end thereof adjacent to the distal extension 40. The seal provides a sliding circumferential seal against the proximal end of catheter body 14 when it is introduced into the central passage 42. The size of the sealing member can be selected to assure substantially complete blockage of any leakage of the inflation media introduced through the port 24 into the central passage 42. Sealing member 50 is configured and positioned so that pressure in the chamber 42 further compresses seal member 50 to enhance the circumferential seal formed against the outside of the catheter body.

Figure 5A:
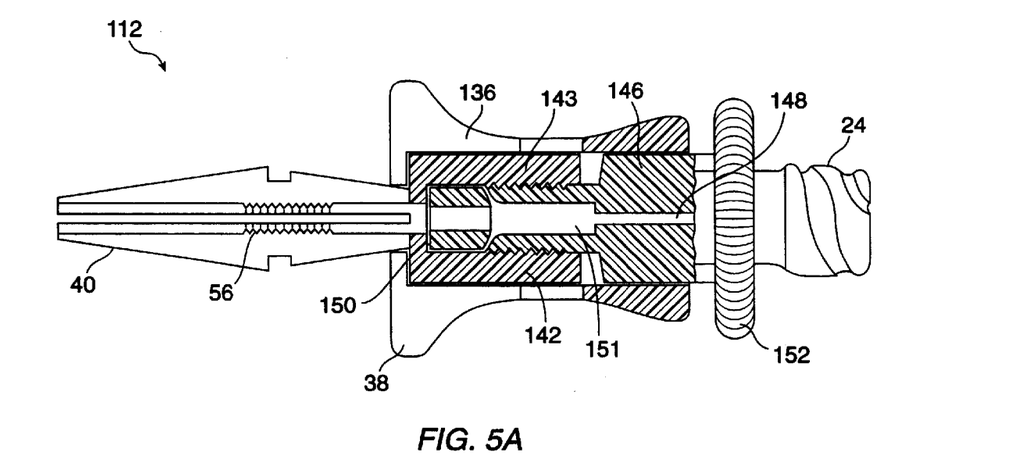
FIG. 5A is a partial cross-sectional view of a hub similar to that illustrated in FIG. 5 and having an axially compressible seal for circumferentially sealing the catheter body.

An alternative hub 112 construction is illustrated in FIG. 5A. The hub 112 is similar in most respects to hub 12 shown in FIGS. 5 and 6, and all like components will be given the same numbers. In place of block 36, however, hub 112 comprises a cup-shaped block member 136 having the distal extension 40 extending from its distal end. Elastomeric sealing member 150 is disposed at a distal end of a central passage 142. A proximal portion of the central passage is threaded and receives a threaded stem 143 on the distal end of rotatable plug 146. The plug 146 includes a proximal passage 148 aligned with but having a smaller diameter than an inflation chamber in the form of a distal passage 151 (defining an inflation chamber within the cup-shaped block member 136 equivalent to passageway 42 of FIG. 5) through the stem of the plug. Conveniently, a rotation ring 152 is disposed on the proximal end of the plug 146 to permit manual rotation. Such manual rotation causes axial translation of the stem 143 which engages and axially compresses (or releases) the elastomeric sealing member 150. In this way, the sealing member can be tightly compressed over a catheter body received in distal passage 151 of the stem.

Figure 5B:
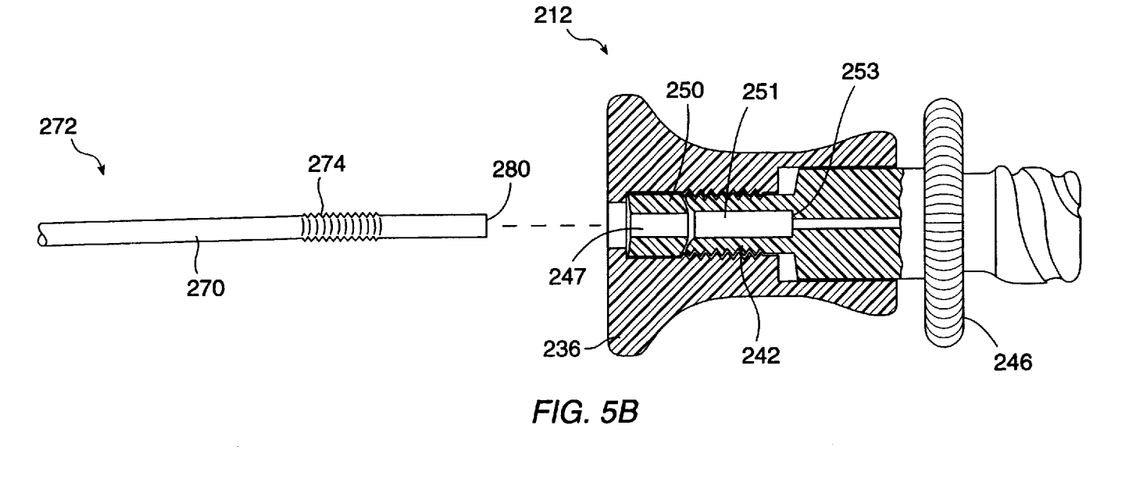
FIG. 5B is a partial cross-sectional view similar to those of FIGS. 5 and 5A, showing an axially compressible seal in combination with a catheter having a surface feature that mechanically interlocks with the compressible seal.

Another alternative hub 212 construction is shown in FIG. 5B. The hub 212 is similar in certain respects to hub 112, except that the circumferential seal component and the mechanical interlock are provided by an elastomeric sealing member 250. The elastomeric seal 250 is axially compressed by rotatable plug 246 which is threadably received in central passage 242 of hub block 236. Rotation of the plug 246 selectively compresses or releases aperture 247 through the seal over exterior surface 270 of catheter 272 when the catheter is received in axial chamber 251 of the plug. In particular, the seal member 247 can be constricted over and mechanically interlocked over a surface feature 274 on the catheter 272, where the feature is properly aligned with the seal member when proximal end 280 of the catheter engages stop 253 (shown as a reduced diameter shoulder) in the chamber 251. Optionally, the inner surface of aperture 247 could be roughened or otherwise modified to provide a surface or surface feature which mates with the surface feature 274 on the catheter when the seal is radially constricted with the plug 246. In this way, both a circumferential seal and a mechanical interlock can be provided. Usually, it will be insufficient to provide just a compressible seal in the hub without modifying the catheter to provide a positive mechanical interlock with the catheter.

Referring again to FIGS. 5 and 6, in addition to the fluid seal provided by sealing member 50 of hub 12, the removable hub includes a mechanism for engaging and securing the proximal end 18 of catheter body 14. The mechanism is provided by distal extension 40 which includes a plurality of cantilevered beams 55 which project forwardly from the cup-shaped block member 136. It will be appreciated that such cantilevered beams define a central passage for receiving the proximal end of the catheter body and may be caused to circumferentially constrict the catheter body when present therein. While such constriction may itself be sufficient to engage and hold the catheter body, the friction can be enhanced by providing a surface feature, such as annular serrations 56, on the interior surface of the beams 55 of distal extension 40. The beams 55 of the distal extension 40 may be circumferentially constricted by sliding the slider 38 distally forward from the proximally retracted configuration of FIG. 5 to the configuration of FIG. 6. Preferably, the proximal end 18 of catheter body 14 will be provided with mating annular serrations 60 or another anchor feature, such as fine pitch threads or a roughened surface, which further assure that the catheter body will be gripped and immobilized by the interlock mechanism of the hub. The proximal port 24 in the removable hub may be attached to a conventional inflation device, such as a syringe or indeflator, by means of a Luer lock. (See FIG. 7).

Figure 7:
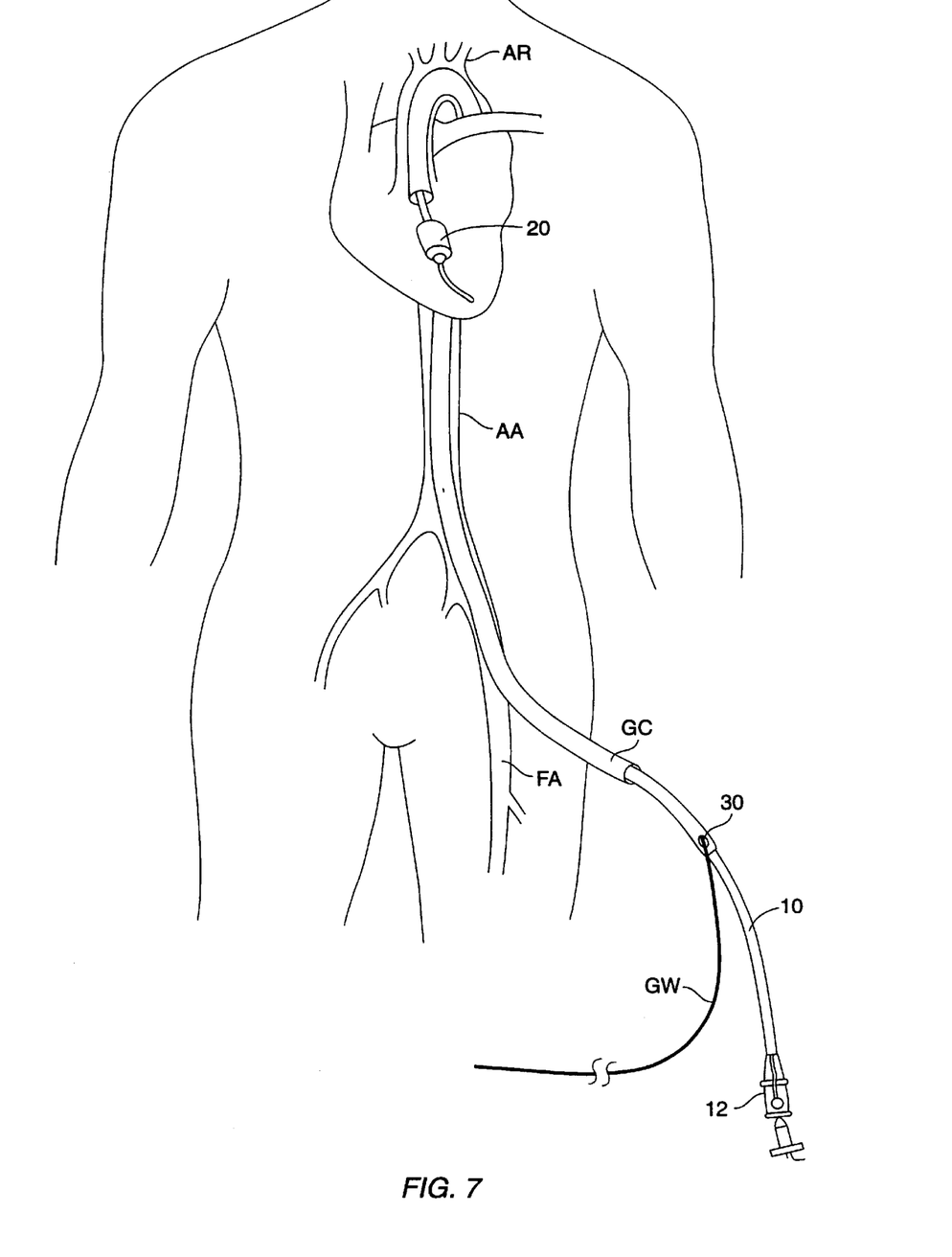
FIG. 7 illustrates the balloon catheter of FIG. 1 introduced through a guiding catheter to a patient's coronary vasculature.

The balloon catheter 10 having the removable hub 12 attached thereto is introduced to a target site in a conventional manner, as illustrated in FIG. 7. In particular, the balloon catheter 10 is introduced through a guiding catheter GC through a hemostatic valve and sheath (not shown) and into the coronary vasculature through the femoral artery (FA), abdominal aorta AA, and aortic arch AR. The balloon 20 will be inflated at a target site in the usual manner, and thereafter deflated. As illustrated, the guide wire GW is shown exiting through proximal port 30 outside of the guiding catheter GC. Usually, however, the guide wire port 30 will be positioned within the guiding catheter GC with the guide wire GW and balloon catheter 10 exiting the guiding catheter GC separately.

Figure 8:
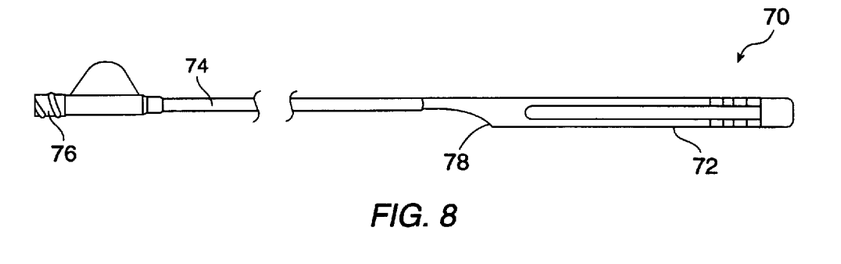
FIG. 8 illustrates an exemplary sleeve catheter having a shortened distal end which may be used in the methods of the present invention.
Figure 9:
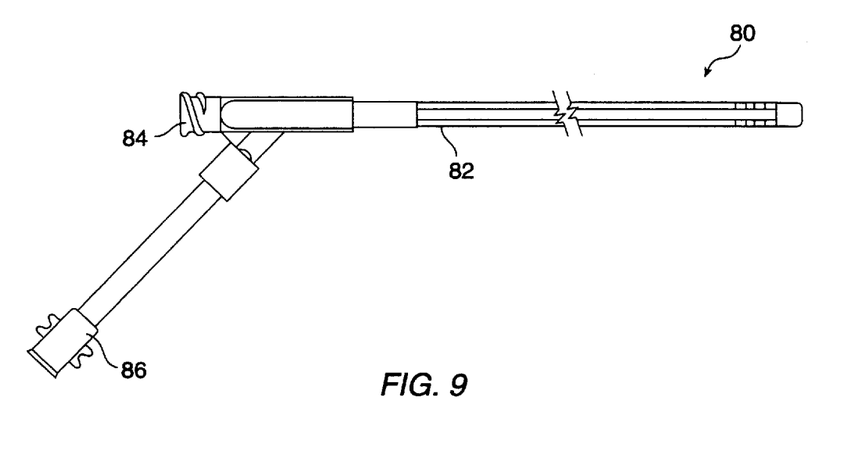
FIG. 9 illustrates a second exemplary sleeve catheter which may be used in the methods of the present invention.

As described thus far, the presence of the removable hub 12 has played no unique role in the deployment of the balloon catheter 10. Referring now to FIGS. 8 and 9, a pair of exemplary sleeve catheters will be described. These sleeve catheters are intended for local drug administration, but it will be appreciated that any of the other sleeve catheters described previously could also be employed. Sleeve catheter 70 shown in FIG. 8 comprises a short sleeve segment 72, a proximal shaft portion 74, and a proximal connector 76 for attaching a fluid infusion source, such as a syringe. The details of construction for such short sleeve catheters are provided in copending application Ser. No. 08/551,932, the full disclosure of which has previously been incorporated herein by reference. Sleeve catheter 80 (FIG. 9) comprises a long sleeve 82 having a proximal port 84 for passing out the balloon catheter. A separate connector 86 is provided for the fluid infusion connection.

Figure 10:
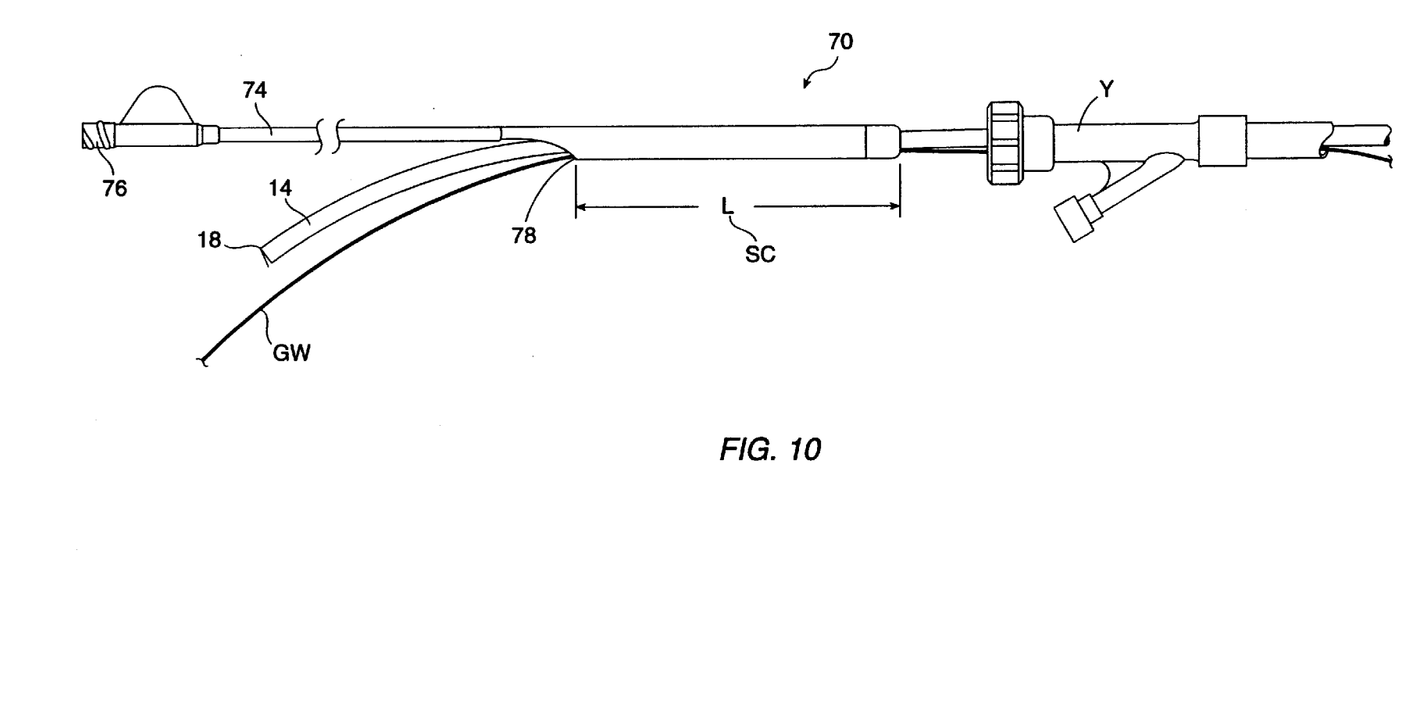
FIG. 10 illustrates mounting of the sleeve catheter of FIG. 8 over the balloon catheter and guide wire of FIG. 7.

Referring now to FIG. 10, mounting of the sleeve catheter 70 over the proximal end 18 of balloon catheter body 14 will be described. The balloon catheter 14 and guide wire GW are present and will remain in the vasculature, as shown in FIG. 7, throughout the entire sleeve catheter exchange procedure(s). The guide wire will be sufficiently long so that it extends proximally of the proximal end 18 of the balloon catheter body 14 by a distance equal to at least the length $L_{BC}$ of the catheter-receiving lumen of catheter 70. Usually, the guide wire will be sufficiently long to extend at least 5 cm beyond the proximal end of the balloon catheter, preferably being 10 cm longer. The proximal end 18 of the balloon catheter body 14 will also extend proximally of the hemostatic valve of the Y connector by a length sufficient to accommodate the $L_{BC}$ of the sleeve catheter 70, usually extending at least 5 cm beyond the Y connector, preferably at least 10 cm beyond the Y connector. The sleeve catheter is then loaded over the proximal end of the balloon catheter by first loading it over the proximal end of the guide wire. The proximal end 18 of the balloon catheter body 14 is then introduced through the distal end of sleeve catheter 70 until it too emerges from proximal port 78. After the proximal ends of both the balloon catheter and guide wire have emerged from port 78 on the sleeve catheter 70, the balloon catheter may be advanced into the hemostatic Y connector valve and through the guide catheter GC (FIG. 7) by pushing on the proximal rod 74 until the distal region is located over the balloon 20.

Although the foregoing invention has been described in detail for purposes of clarity of understanding, it will be obvious that certain modifications may be practiced within the scope of the appended claims.

What is claimed is:

1. A method for introducing a sleeve catheter over a balloon catheter in a patient, said method comprising:

providing a balloon catheter having a distal end, a balloon near the distal end, a proximal end, an inflation lumen extending from the proximal end to the balloon, a guide wire lumen having a distal port and a proximal port, and a hub;

providing a sleeve catheter having a distal end, an interactive device which interacts with the balloon disposed near the distal end of the sleeve catheter, a proximal end, and a central lumen extending from a distal balloon catheter port disposed distally of the interactive device to a proximal balloon catheter port disposed proximally of the interactive device;

wherein the balloon catheter providing step comprises selecting the balloon catheter to have $L_{BC}$, wherein:

$$L_{BC} \geq L_V + L_{SC} + 5 \text{ cm},$$

wherein:

$L_V$=maximum expected length of the balloon catheter in vasculature;

$L_{SC}$=length of the sleeve portion of the sleeve catheter;

percutaneously introducing a guide wire to a target site in a patient's vasculature;

percutaneously advancing the balloon catheter over the guide wire to the target site, wherein the hub is attached to the proximal end of the balloon catheter and wherein the guide wire passes through the guide wire lumen;

inflating the balloon on the balloon catheter at the target site to perform balloon angioplasty;

deflating the balloon;

disengaging and removing the hub while maintaining the guide wire and balloon catheter at the target site in the patient's vasculature;

advancing the distal balloon catheter port of the sleeve catheter over the proximal end of the balloon catheter while the guide wire and balloon catheter remain in place at the target site so that the proximal end of the balloon catheter emerges from the proximal balloon catheter port prior to the distal end of the sleeve catheter entering the guide catheter; and remounting the hub over the proximal end of the balloon catheter.

2. A method as in claim 1, wherein the length of the balloon catheter $L_{BC}$ is in the range from 120 cm to 200 cm.

3. A method as in claim 2, further comprising providing a guide wire, wherein the guide wire is selected to have a length $L_{GW}$, wherein:

$$L_{GW} \geq L_{BC} + 10 \text{ cm}.$$

4. A method as in claim 1, wherein the hub mounting step comprises passing the catheter through a circumferential seal in the hub into an inflation chamber in the hub until the catheter reaches a stop in the chamber; and engaging a locking element on the hub against the catheter body to axially lock the hub relative to the balloon catheter.

5. A method as in claim 4, wherein the locking element engaging step comprises constricting a portion of the hub circumferentially about the catheter body.

6. A method as in claim 5, wherein the constricted portion of the hub comprises a surface feature which grips the surface of the catheter body when constricted thereabout.

7. A method as in claim 6, wherein the catheter body comprises an anchor feature which mates with the surface feature when constricted thereabout.

8. A method as in claim 7, wherein both the surface feature and the anchor feature comprise annular surface serrations which mate when the extension is constricted.

9. A method as in claim 1, further comprising prior to advancing the distal balloon catheter port of the sleeve catheter over the proximal end of the balloon catheter, selecting a sleeve catheter having an interactive element selected from the group consisting of drug infusion lumens, a stent, perfusion lumens, imaging elements, and a balloon enlargement membrane.

* * * * *